United States Patent [19]

Fitz

[11] Patent Number: 5,097,964
[45] Date of Patent: Mar. 24, 1992

[54] DENTAL FLOSS DISPENSER

[76] Inventor: Steven D. Fitz, 448 Canterbury Rd., Bay Village, Ohio 44140

[21] Appl. No.: 647,570

[22] Filed: Jan. 28, 1991

[51] Int. Cl.⁵ .................................................. A47F 7/00
[52] U.S. Cl. ........................................... 211/65; 211/13
[58] Field of Search ............... 248/915, 102, 176, 108, 248/109, 110, 111; 211/65, 66, 13; D6/530; D28/64; 132/3 R

[56] References Cited

U.S. PATENT DOCUMENTS

| | | | |
|---|---|---|---|
| D. 199,557 | 11/1964 | Lefco | D6/530 |
| D. 199,726 | 12/1964 | Hamilton | D6/530 |
| D. 228,188 | 8/1973 | Howison | D28/64 |
| D. 257,402 | 10/1980 | Denton et al. | D28/64 |
| D. 266,194 | 9/1982 | Graves | D28/64 |
| D. 267,060 | 11/1982 | Iwatmoto | D6/530 |
| D. 300,961 | 5/1989 | Woodman et al. | D28/64 |
| 2,415,447 | 2/1947 | Stanton | 211/65 X |
| 2,471,680 | 5/1949 | Gibson, Jr. | 211/65 X |
| 2,771,219 | 11/1956 | Deney | 248/176 X |
| 2,967,651 | 1/1961 | Zackheim et al. | D28/64 X |
| 3,246,815 | 4/1966 | Aronson | D28/64 X |
| 3,519,004 | 7/1970 | Foster | 132/92 |
| 3,525,461 | 8/1970 | Freedman | 225/21 |
| 3,592,203 | 7/1971 | Johnson | 132/91 |
| 3,746,225 | 7/1973 | Runckel | 225/19 |
| 3,747,611 | 7/1973 | Bennington | 132/91 |
| 3,759,272 | 9/1973 | Di Vincenti | 132/92 R |
| 3,759,273 | 9/1973 | Knaus | 132/92 R |
| 3,782,397 | 1/1974 | McCord | 132/84 A |
| 3,804,102 | 4/1974 | Bennington | 132/92 A |
| 3,833,009 | 9/1974 | Bennington | 132/91 |
| 3,870,059 | 3/1975 | Bennington | 132/92 A |
| 3,881,502 | 5/1975 | Bennington | 132/91 |
| 4,031,909 | 6/1977 | Kelley | 132/91 |
| 4,286,611 | 9/1981 | Talbot | 132/91 |
| 4,308,880 | 1/1982 | Graves | 132/321 |
| 4,327,755 | 5/1982 | Endelson | 132/92 R |
| 4,428,389 | 1/1984 | Cordero | 132/92 A |
| 4,635,660 | 1/1987 | Graves | 132/92 A |
| 4,671,307 | 6/1987 | Curbow et al. | 132/91 |
| 4,673,106 | 6/1987 | Fishman | 222/80 |
| 4,706,694 | 11/1987 | Lambert | 132/92 R |
| 4,706,695 | 11/1987 | Urso | 132/92 R |
| 4,738,271 | 4/1988 | Bianco | 132/92 R |
| 4,788,990 | 12/1988 | Wisegerber | 132/324 |
| 4,796,783 | 1/1989 | Paulson | 222/80 |
| 4,844,104 | 7/1989 | Martin | 132/321 |

FOREIGN PATENT DOCUMENTS 1273213  11/1960  France ............... D28/64

Primary Examiner—Carl D. Friedman
Assistant Examiner—Sarah A. Lechok
Attorney, Agent, or Firm—Renner, Otto, Boisselle & Sklar

[57] ABSTRACT

A dental floss dispenser is described which is characterized by a hollow housing having an outer appearance reminiscent of a character appealing to the potential user of the disperser. The housing has a passageway for passing floss from inside the housing to outside the housing. An appendage on the housing, preferably in the form of a pair of teeth, has an aperture in the form of a slotted space for passing floss therethrough. A cutter mounted elsewhere on the housing is used for cutting the floss.

19 Claims, 3 Drawing Sheets 5,097,964

DENTAL FLOSS DISPENSER

FIELD OF THE INVENTION

This invention relates to dental floss dispensers. In particular, this invention relates to a floss dispenser in which the housing is in the shape of a character.

BACKGROUND OF THE INVENTION

Periodic use of dental floss for disorganizing bacterial plaque near the gum line and between teeth and for stimulating circulation in the gums is recommended for good oral hygiene. Various dental floss dispensers are commercially available, but generally have been merely storage and dispensing devices for floss. Few have been formed in such a way as to encourage the flossing process, especially for children and young adults.

SUMMARY OF THE INVENTION

The present invention provides a convenient dispenser for dental floss formed in such a way as to encourage flossing and to make the flossing process more enjoyable. The dispenser includes a hollow housing having an outer appearance reminiscent of some character appealing to the potential user of the dispenser. The housing has an outside surface and a passageway for passing floss from inside the housing to outside the housing. An appendage on the housing, preferably in the form of two teeth, has an aperture in the form of a slotted space for passing the flows therethrough. A cutter mounted elsewhere on the housing is used for cutting the floss.

After the floss is cut, it remains wedged under the cutter blade or dangles from the slot in the appendage. The user pulls on the floss, drawing the floss out of the housing and through the slot. When the slotted appendage resembles a pair of teeth, the act of withdrawing the floss from the dispenser simulates flossing. The association between flossing and the appealing character represented by the dispenser helps motivate children and young adults to floss.

When the dispenser housing is shaped in such a manner that it can be stood upright on a flat surface, or adhered to a wall or mirror, then the dispenser, by virtue of its appealing appearance, may serve as a daily reminder to people of all ages.

To accomplish the foregoing ends, the invention comprises the features hereinafter fully described and particularly pointed out in the claims, the following description and the annexed drawings setting forth in detail a certain illustrative embodiment of the invention, this being indicative, however, of but one of the various ways in which the principles of the invention may be employed.

DETAILED DESCRIPTION OF THE INVENTION

Figure 1:
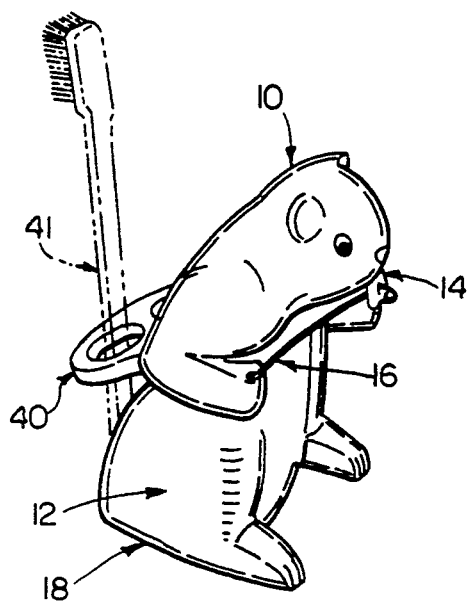
FIG. 1 is a perspective view of a floss dispenser according to the present invention.

The invention may be illustrated by reference to one embodiment depicted in FIGS. 1-13. FIG. 1 shows a dental floss dispenser 10 comprising a dispenser housing 12 which resembles a beaver in the upright position having a pair of teeth 14 through which a length of floss 16 may be threaded. A tail adapted to function as a toothbrush holder 40 may be integrally formed with the housing 12. FIG. 1 illustrates a how a toothbrush 41 may be inserted through the toothbrush holder tail 40. The toothbrush 41 is shown only for illustration of the function of the toothbrush holder 40. The toothbrush 41 is not considered to be a required element of this embodiment.

Figure 2:
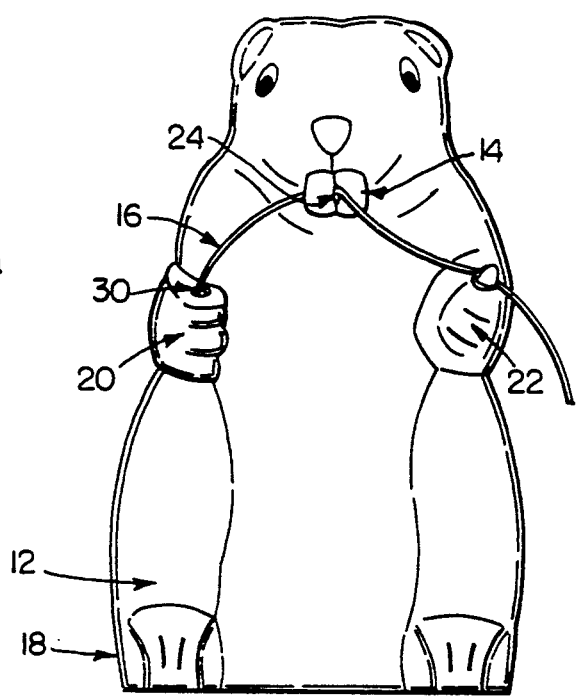
FIG. 2 is a front view of the floss dispenser shown in FIG. 1.
Figure 3:
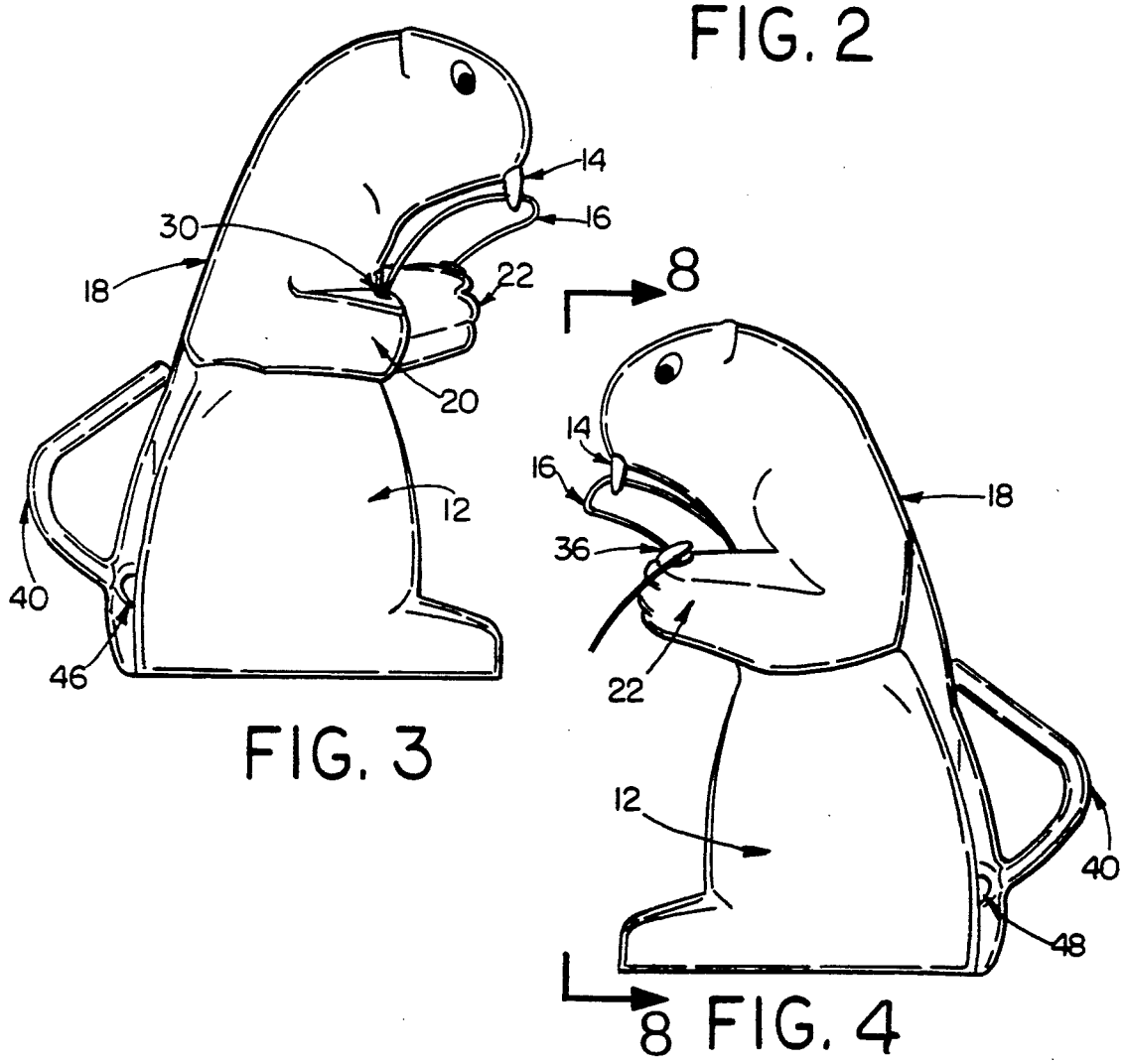
FIG. 3 is a right side view of the floss dispenser shown in FIG. 1.
Figure 4:
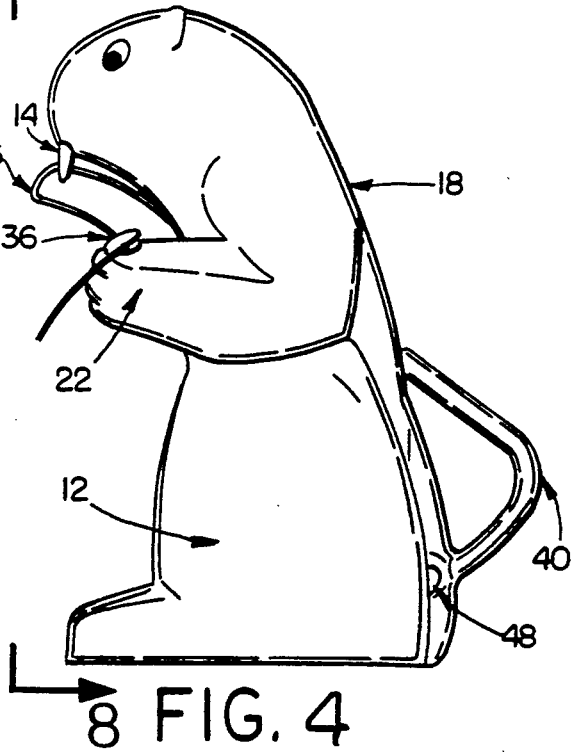
FIG. 4 is a left side view of the floss dispenser shown in FIG. 1.

FIGS. 2-4 provide front, right side, and left side views of dispenser 10 shown in FIG. 1. These figures show right paw 20 and left paw 22 extending outwardly at substantially the same level below teeth 14. Right paw 20 comprises a passage between the interior and exterior of housing 12 through which the floss 16 may be threaded. The floss 16 then passes through a slot 24 located between the pair of teeth 14. A cutter 36 mounted on left paw 22 engages the floss 16 in order to hold and cut the floss 16. FIGS. 3 and 4 illustrate how the toothbrush holder tail 40 is integrally formed with the housing 12 and shown openings 46 and 48 described in greater detail below in connection with FIGS. 5 and 6.

Figure 5:
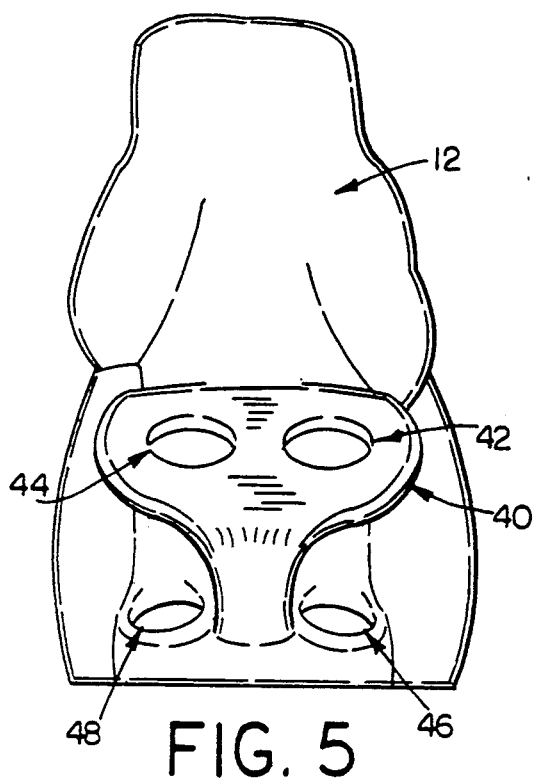
FIG. 5 is a rear view of the floss dispenser shown in FIG. 1.
Figure 6:
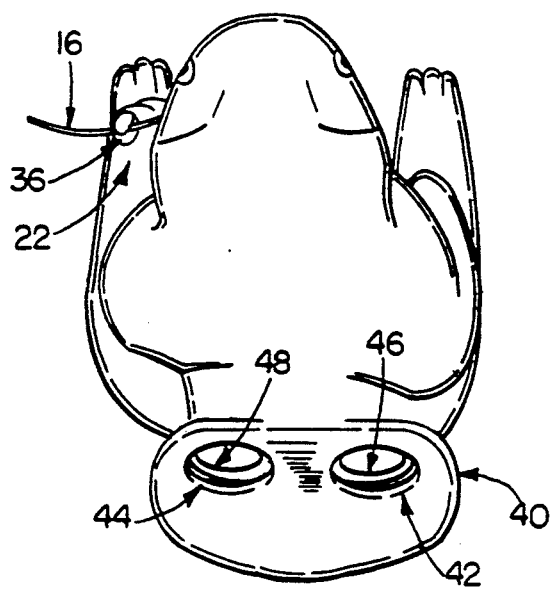
FIG. 6 is a top view of the floss dispenser shown in FIG. 1.

FIGS. 5 and 6 provide a rear view and top view of the dispenser 10 of FIG. 1. These views show the toothbrush holder tail 40 in greater detail. The toothbrush holder tail 40 comprises a first opening 42, a second opening 44, a third opening 46, and a fourth opening 48. The first opening 42 is substantially vertically aligned with the third opening 46 and the second opening 44 is substantially vertically aligned with the fourth opening 48. Openings 46 and 48 are of sufficient width and depth to retain the end of a typical toothbrush handle.

Figure 7:
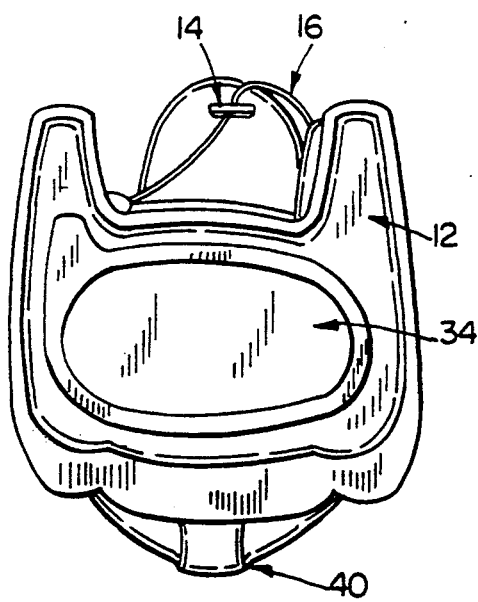
FIG. 7 is a bottom view of the floss dispenser shown in FIG. 1.

FIG. 7 shows a bottom view of the dispenser 10 of FIG. 1. The bottom comprises a removable lid 34 engaged in the housing 12.

Figure 8:
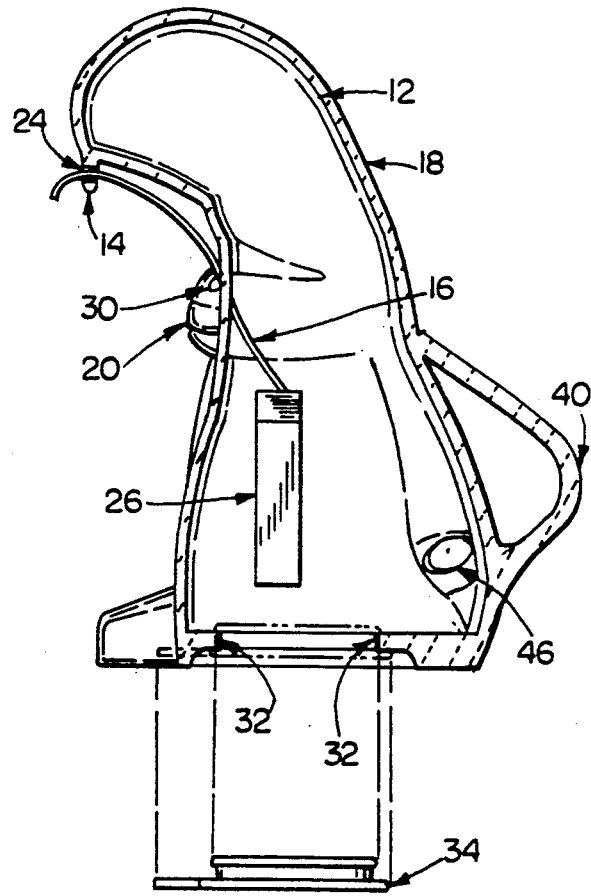
FIG. 8 is a cross-sectional view of the floss dispenser shown in FIG. 4.

FIG. 8 shows a cross-sectional view of the floss dispenser shown in FIG. 4. This view shows the floss 16 originating from a supply spool 26, which in this case is an ordinary disposable floss dispensing container available in this case in an ordinary disposable floss dispensing container available in any store in which dental hygiene products are sold. The floss 16 passes from inside the housing 12 through the passageway 30 in right paw 20 until it is outside the housing 12. The floss 16 then passes through slot 24 between the pair of teeth 14. The lid 34 is shown removed from opening 32 in the housing 12. Removal of lid 34 permits replacement of the supply spool 26 through the opening 32 when the supply of floss 16 is exhausted.

Figure 9:
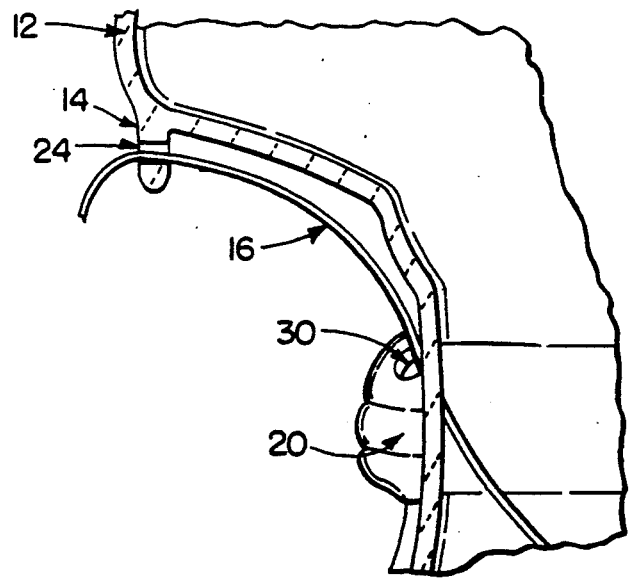
FIG. 9 is a detailed cross-sectional view of the portion of the floss dispenser shown in FIG. 4 through which the floss passes from inside the dispenser to the externally mounted teeth.
Figure 13:
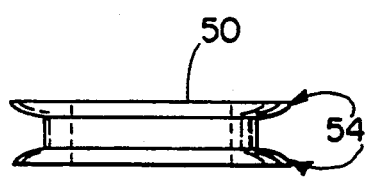
FIG. 13 is a side view of the toothbrush holding device of FIG. 12.

FIG. 9 is a detailed cross-sectional view of the portion of the floss dispenser shown in FIG. 4 through which the floss 16 passes from inside the dispenser through passageway 30 to the externally mounted teeth 14.

In practice, the user pulls a desired length of floss 16 from the dispenser 10, which may then be cut with the cutter 36. As one may appreciate, the position of the teeth 14 above the paws 20 and 22 allows the user to pull the floss 16 to the desired length with one left to right movement.

Preferably, the cutter 36 is of a type which retains the end of the floss after it is cut to enhance the image of the character holding floss in tension between its paws to "floss" its teeth.

Figure 10:
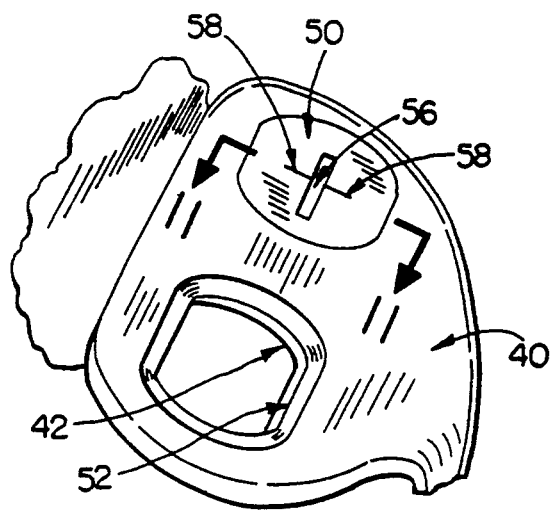
FIG. 10 is a detailed view of an alternate embodiment of the toothbrush holding portion of the floss dispenser shown in FIG. 1 showing the opening in which a toothbrush holding device is engaged.
Figure 11:
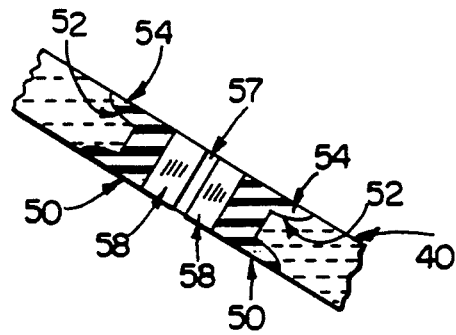
FIG. 11 is a cross-sectional view of the toothbrush holding portion of the floss dispenser shown in FIG. 10 showing the toothbrush device fully engaged in the opening.
Figure 12:
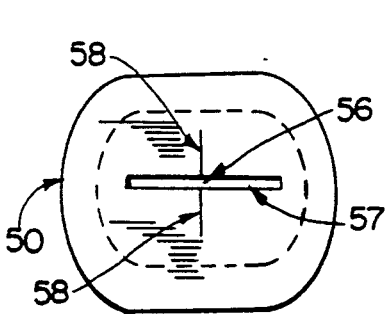
FIG. 12 is a top view of the toothbrush holding device of FIG. 11.

FIGS. 10-13 show a detailed view of an alternative embodiment of the toothbrush holding portion of the floss dispenser 40 which uses a toothbrush holding lug 50. In this embodiment, toothbrush holding plug 50 is present in each of first opening 42 and second opening 44 in the toothbrush holding tail 40. FIG. 10 shows the toothbrush holding tail 40 with one toothbrush holding plug 50 removed to show the first opening 42 in the toothbrush holding tail 40 into which the toothbrush holding plug 50 is inserted. The opening 42 has an indented mating surface 52 for engaging plug 50 as shown in the FIG. 11 cross-sectional view of opening 42 with plug 50 inserted. FIG. 11, shows that when plug 50 is inserted into opening 42, flanged portions 54 of the toothbrush holding plug 50 engage with a mating surface 52 of the toothbrush holding tail 40. The resilience of plug 50 permits the flange 54 to be forced past the mating surface 52 in order to position plug 50 flush with the surface of toothbrush holding tail 40.

Each plug 50 comprises an expandable opening 56 for accepting the handle of a toothbrush. In this embodiment, the expandable opening 56 comprises a horizontal slot 57 intersecting a vertical cut 58 approximately in the center of the plug 50. The slot 57 and cut 58 permit expansion in more than one direction to accommodate various toothbrush handle cross-sections and yet firmly hold a toothbrush handle.

Other expandable opening shapes such as elongated slits, star-shape, inward-pointing finger-like projections, and oval expandable openings may be utilized as the expandable opening.

Examples of elastomeric materials from which plug 50 may be made include vulcanized rubber, such as the commercially available vulcanized synthetic or gum rubbers, silicone rubber, etc. Preferably, the elastomeric material is hypo-allergenic and resistant to deterioration or loss of resiliency.

When the toothbrush holding tail 40 comprises toothbrush holding plug 50, the third opening 46 and fourth opening 48 depicted in FIGS. 3-6 and 8 are optional since plug 50 can be sufficient to hold the toothbrush 41 upright.

The dispenser 10 may be made of ceramic, plastic, metal, etc., and may be colored with various pigments and augmented with various functional and/or ornamental features attached to, or integrally formed with, the housing. The lid 34 may be plastic or any other suitable material to permit easy removal and replacement of an empty spool of floss.

A convenient way to "rethread" the illustrated dispenser is to tie the end of the floss from the old spool onto the beginning end of the floss in the new spool and then pulling the floss out through passageway 30 until the floss from the new spool is threaded through slot 24.

In another embodiment, the housing is of a two-piece construction to allow easy access to the interior of the housing, including access to passageway 30 from inside the housing to facilitate "threading" of the floss through passageway 30 from the inside. The two pieces may be detachable from each other or connected by one or more pivot points acting as a hinge.

A detachable two-piece housing may, for instance, be formed such that each has male and female mating surfaces that engage due to friction caused by a tight fit or engage in a snap coupling action due to coupling action of a resilient engaging member. The resilient engaging member may, for example, be a flange having a concave or protruding area integrally formed with the inside of the female coupling member or the outside of the male coupling member that engages with a corresponding flange having a convex or protruding area integrally formed with the outside of the male coupling member or the inside of the female coupling member, respectively. The female and/or male coupling members are preferably sufficiently elastic and resilient to permit the respective coupling areas to slide over or past each other such that the respective pieces become coupled or engaged. Coupling may also be achieved by using flanges which engage each other and hold the two-piece housing together when one piece is turned or twisted relative to other. Numerous other engaging means are well known and within the purview of those of ordinary skill in the art of making two-piece easily detachable and recoupled constructions.

In yet another embodiment, the dispenser is made of an economically mass-produced material, such as a plastic, such that it may be disposed of when the floss runs out. Such dispensers would not require any means for opening and reclosing the dispenser.

The character depicted in the drawings is in the likeness of a beaver. However, the character of the present invention is not limited to that embodiment. A wide range of characters is intended to be within the general concept of the invention. Other embodiments include fantasy or fictional characters such as robots, "monsters", cartoon characters; various characters seen in movie and television programing; characters of human likeness; other members of the animal kingdom such as a gopher, mouse or rabbit, etc. Characters having anthropomorphic characteristics are generally preferred and the ability to hold one or more toothbrushes is optional.

Although the invention has been shown and described with respect to a certain preferred embodiment, it is obvious that equivalent alternations and modifications will occur to others skilled in the art upon reading and understanding of the specification. The present invention includes all such equivalent alternations and modifications and is limited only by the scope of the following claims.

What is claimed is:

1. A dental floss dispenser for dispensing floss, comprising:
   a hollow housing for holding said floss and having an outside surface in a shape reminiscent of a toothed character;
   a passageway for passing said floss from inside said housing to outside said housing;
   an appendage attached to the outside of said housing having a slot therein for threading floss therethrough; and
   a cutter mounted on said outside surface of said housing for cutting floss;
   wherein said appendage simulates a pair of teeth of said character and wherein said slot is a slotted space between said teeth of said simulated pair of teeth.

2. The floss dispenser of claim 1 wherein said passageway and said cutter are in horizontally spaced relation to one an other and said slot is in spaced relation between said passageway and said cutter.

3. The floss dispenser of claim 2 wherein said slot is located in spaced relation above said passageway and said cutter.

4. The floss dispenser of claim 1 wherein said housing is shaped in the likeness of an anthropomorphic character.

5. The floss dispenser of claim 1 wherein said housing is shaped in the likeness of a member of the animal kingdom.

6. The floss dispenser of claim 5 wherein said member of the animal kingdom is a beaver.

7. The floss dispenser of claim 6 wherein said housing includes two paws extended outwardly at substantially equal level, said cutter is positioned on one of said paws and said passageway is positioned on the other paw.

8. The floss dispenser of claim 7 wherein said slot is located in spaced relation above said passageway and said cutter.

9. The floss dispenser of claim 1 further comprising toothbrush holding means integrally formed with said housing for holding a toothbrush.

10. The floss dispenser of claim 9 wherein said housing is shaped in the likeness of a member of the animal kingdom.

11. The floss dispenser of claim 10 wherein said member of the animal kingdom is a beaver and wherein said toothbrush holding means simulates a tail rigidly mounted on said housing having at least one opening therein for accepting the handle of a toothbrush.

12. The floss dispenser of claim 11 wherein said housing comprises an opening for accepting the end of a toothbrush handle substantially vertically aligned below one of the at least one opening in the tail.

13. In combination, The floss dispenser of claim 1 and a spool of floss stored inside said housing, and an end section of floss from spool passing through said passageway and said slot.

14. A dental floss dispenser for dispensing floss, comprising:
   a hollow housing for holding said floss and having an outside surface;
   a passageway for passing said floss from inside said housing to outside said housing;
   a first appendage attached to the outside of said housing having a slot therein for threading floss therethrough; and
   a second appendage having a distal end relative to said housing attached to said outside surface of said housing having a cutter mounted on said distal end thereof for cutting floss wherein said passageway and said cutter are in horizontally spaced relation to one another and said slot is in spaced relation above said passageway and said cutter.

15. The floss dispenser of claim 14 wherein said appendage simulates a pair of teeth and wherein said slot is a slotted space between said teeth of said simulated pair of teeth.

16. The floss dispenser of claim 14 wherein said housing is shaped in the likeness of a member of the animal kingdom.

17. The floss dispenser of claim 16 wherein said member of the animal kingdom is a beaver.

18. The floss dispenser of claim 17 wherein said housing includes two paws extended outwardly at substantially equal level such that one of said paws corresponds to said second appendage, said cutter positioned at the distal end thereof, and said passageway is positioned on the other paw.

19. The floss dispenser of claim 14 further comprising toothbrush holding means integrally formed with said housing.

* * * * *